United States Patent [19]

Komada et al.

[11] Patent Number: 6,143,690
[45] Date of Patent: Nov. 7, 2000

[54] AMMOXIDATION CATALYST FOR USE IN PRODUCING ACRYLONITRILE OR METHACRYLONITRILE FROM PROPANE OR ISOBUTANE

[75] Inventors: Satoru Komada; Masatoshi Kaneta, both of Yokohama, Japan

[73] Assignee: Asahi Kasei Kogyo Kabushiki Kaisha, Osaka, Japan

[21] Appl. No.: 09/304,956

[22] Filed: May 5, 1999

[30] Foreign Application Priority Data

May 7, 1998 [JP] Japan .................................. 10-139221

[51] Int. Cl.[7] .......................... B01J 27/19; C07C 253/24
[52] U.S. Cl. ......................... 502/211; 502/312; 558/318; 558/319
[58] Field of Search ................... 558/318, 319; 502/211, 312

[56] References Cited

U.S. PATENT DOCUMENTS 5,422,328  6/1995  Ushikubo et al. ...................... 502/312

FOREIGN PATENT DOCUMENTS 767 164 A1  4/1997  European Pat. Off. .
7-144132    6/1995  Japan .
8-57319     3/1996  Japan .
8-141401    6/1996  Japan .
10-28862    2/1998  Japan .

*Primary Examiner*—Joseph K. McKane
*Assistant Examiner*—Ebenezer Sackey
*Attorney, Agent, or Firm*—Birch, Stewart, Kolasch & Birch LLP

[57] ABSTRACT

An ammoxidation catalyst for use in producing acrylonitrile or methacrylonitrile from propane or isobutane, which comprises a compound oxide and a silica carrier having supported thereon the compound oxide, wherein the compound oxide comprises molybdenum, vanadium, niobium and at least one element selected from the group consisting of tellurium and antimony, and wherein the alkali metal content of the ammoxidation catalyst is extremely small or substantially zero, and a process for producing acrylonitrile or methacrylonitrile by using the ammoxidation catalyst. By the use of the ammoxidation catalyst of the present invention, acrylonitrile or methacrylonitrile can be produced in high yield, as compared to the yield achieved by conventional ammoxidation catalysts containing a silica carrier.

12 Claims, No Drawings

AMMOXIDATION CATALYST FOR USE IN PRODUCING ACRYLONITRILE OR METHACRYLONITRILE FROM PROPANE OR ISOBUTANE

BACKGROUND OF THE INVENTION

1. Field of the Invention

The present invention relates to an ammoxidation catalyst for use in producing acrylonitrile or methacrylonitrile from propane or isobutane. More particularly, the present invention is concerned with an ammoxidation catalyst comprising a compound oxide and a silica carrier having supported thereon the compound oxide, wherein the compound oxide comprises molybdenum, vanadium, niobium and at least one element selected from the group consisting of tellurium and antimony, and wherein the alkali metal content of the ammoxidation catalyst is extremely small or substantially zero. By the use of the ammoxidation catalyst of the present invention, acrylonitrile or methacrylonitrile can be produced in high yield, as compared to the yield achieved by conventional ammoxidation catalysts containing a silica carrier. The present invention is also concerned with a process for producing acrylonitrile or methacrylonitrile by using such an excellent ammoxidation catalyst.

2. Prior art

A process for producing acrylonitrile or methacrylonitrile by ammoxidation of propylene or isobutylene has been well-known. Recently, as a substitute for such a process using propylene or isobutene, a process for producing acrylonitrile or methacrylonitrile by gaseous phase catalytic ammoxidation of propane or isobutane, i.e., by gaseous phase catalytic reaction of propane or isobutane with ammonia and molecular oxygen has attracted attention.

With respect to catalysts for use in producing acrylonitrile or methacrylonitrile from propane or isobutane by ammoxidation, a number of proposals have been made. For example, as a catalyst for use in the ammoxidation of an alkane, oxide catalysts containing molybdenum, vanadium, niobium and tellurium are disclosed in EP 0 529 853 B1, U.S. Pat. No. 5,049,692, U.S. Pat. No. 5,231,214, U.S. Pat. No. 5,422,328, Unexamined Japanese Patent Application Laid-Open Specification Nos. 7-144132, 7-289907, 8-57319, 8-141401 and 10-28862.

Further, oxide catalysts containing molybdenum, vanadium, niobium and antimony are disclosed in, for example, EP 0 767 164 A1, U.S. Pat. No. 4,760,159, U.S. Pat. No. 4,797,381, Unexamined Japanese Patent Application Laid-Open Specification Nos. 5-213848 and 10-28862.

Thus, in the art, an oxide catalyst containing molybdenum, vanadium, niobium and at least one element selected from the group consisting of tellurium and antimony has attracted attention as a promising ammoxidation catalyst for producing an unsaturated nitrile from an alkane in high yield.

Generally, when an unsaturated nitrile, such as acrylonitrile or methacrylonitrile, is produced by ammoxidation on a commercial scale, the ammoxidation is conducted using a fluidized-bed reactor. With respect to a catalyst for the ammoxidation using a fluidized-bed reactor, it is necessary for the ammoxidation catalyst to have a high attrition resistance. For this reason, an ammoxidation catalyst conventionally has a structure wherein a compound oxide is supported on a silica carrier so as to provide an attrition resistance. However, with respect to conventional ammoxidation catalysts which comprise a compound oxide and a silica carrier having supported thereon the compound oxide, wherein the compound oxide contains molybdenum (Mo), vanadium (V), niobium (Nb) and at least one element selected from the group consisting of tellurium (Te) and antimony (Sb), there has been a problem in that, when the silica carrier is employed in an amount necessary for imparting a satisfactory attrition resistance to the catalyst, the yield of the desired unsaturated nitrile is likely to become low (the reason for this problem has not yet been elucidated). Therefore, various attempts have been made for solving this problem (i.e., for achieving a high yield of the desired unsaturated nitrile in the ammoxidation of an alkane even when using an oxide catalyst comprising a silica carrier having supported thereon a compound oxide of the above specific metallic elements).

For example, Unexamined Japanese Patent Application Laid-Open Specification No. 8-57319 discloses a method for producing an ammoxidation catalyst for use in producing acrylonitrile from propane, wherein the catalyst comprises a silica carrier having supported thereon a compound oxide of Mo, V, Nb and Te, in which the silica carrier is present in an amount of from 30 to 50% by weight, based on the total weight of the compound oxide and the silica carrier. In this prior art technique, for improving the acrylonitrile yield in the ammoxidation of propane, the catalyst is treated with an acid in order to activate the catalyst. However, this technique is disadvantageous not only in that a cumbersome operation for the acid treatment of the catalyst is required, but also the waste acid produced by the acid treatment of the catalyst must be disposed of properly. Thus, this prior art technique is disadvantageous from a commercial viewpoint.

Therefore, it has been desired to develop an improved ammoxidation catalyst comprising a silica carrier having supported thereon a compound oxide of Mo, V, Nb and at least one element selected from the group consisting of Te and Sb, which is not only effective for producing acrylonitrile or methacrylonitrile in high yield, as compared to the yield achieved by conventional ammoxidation catalysts containing a silica carrier, but also can be easily produced, so that it is advantageous from a commercial viewpoint.

SUMMARY OF THE INVENTION

In this situation, the present inventors have conducted extensive and intensive studies with a view toward developing an improved catalyst for use in producing acrylonitrile or methacrylonitrile from propane or isobutane by ammoxidation in the gaseous phase, which is not only effective for producing acrylonitrile or methacrylonitrile in high yield, as compared to the yield achieved by conventional ammoxidation catalysts containing a silica carrier, but also can be easily produced. As a result, it has unexpectedly been found that the above objective can be attained by an ammoxidation catalyst comprising a compound oxide and a silica carrier having supported thereon the compound oxide, wherein the compound oxide comprises molybdenum, vanadium, niobium and at least one element selected from the group consisting of tellurium and antimony, and wherein the alkali metal content of the ammoxidation catalyst is extremely small or substantially zero. The present invention has been completed, based on the above novel finding.

Accordingly, it is an object of the present invention to provide an ammoxidation catalyst for use in producing acrylonitrile or methacrylonitrile from propane or isobutane by ammoxidation in the gaseous phase, which is commercially advantageous not only in that acrylonitrile or methacrylonitrile can be produced in high yield, as compared to the yield achieved by conventional ammoxidation catalysts containing a silica carrier, but also in that the catalyst can be easily produced.

It is another object of the present invention to provide a process for producing acrylonitrile or methacrylonitrile from propane or isobutane by ammoxidation in the gaseous phase, using such an excellent catalyst.

The foregoing and other objects, features and advantages of the present invention will be apparent to those skilled in the art from the following detailed description taken in connection with the appended claims.

DETAILED DESCRIPTION OF THE INVENTION

In one aspect of the present invention, there is provided an ammoxidation catalyst for use in producing acrylonitrile or methacrylonitrile from propane or isobutane by ammoxidation in the gaseous phase, which comprises a compound oxide and a silica carrier having supported thereon the compound oxide, the compound oxide comprising molybdenum (Mo), vanadium (V), niobium (Nb) and at least one element selected from the group consisting of tellurium and antimony, wherein the catalyst has an alkali metal content of 0.01 or less in terms of the atomic ratio of an alkali metal, relative to molybdenum.

In another aspect of the present invention, there is provided a process for producing acrylonitrile or methacrylonitrile, which comprises reacting propane or isobutane with ammonia and molecular oxygen in the gaseous phase in the presence of the catalyst defined above.

For an easy understanding of the present invention, the features and various preferred embodiments of the present invention are enumerated below.

1. An ammoxidation catalyst for use in producing acrylonitrile or methacrylonitrile from propane or isobutane by ammoxidation in the gaseous phase, which comprises a compound oxide and a silica carrier having supported thereon the compound oxide, the compound oxide comprising molybdenum (Mo), vanadium (V), niobium (Nb) and at least one element selected from the group consisting of tellurium and antimony, wherein the catalyst has an alkali metal content of 0.01 or less in terms of the atomic ratio of an alkali metal, relative to molybdenum.

2. The catalyst according to item 1 above, wherein the silica carrier is present in an amount of from 25 to 70% by weight in terms of $SiO_2$, based on the total weight of the compound oxide and the silica carrier, and wherein the compound oxide is represented by the following formula (1):

$$Mo_{1.0}V_aNb_bX_cZ_dO_n \qquad (1)$$

wherein:

X is at least one element selected from the group consisting of tellurium and antimony;

Z is at least one element selected from the group consisting of ytterbium, dysprosium, erbium, cerium, neodymium, samarium, lanthanum, praseodymium, europium, gadolinium, terbium, holmium, thulium, lutetium, scandium, tungsten, chromium, tantalum, titanium, zirconium, hafnium, manganese, rhenium, iron, ruthenium, cobalt, rhodium, nickel, palladium, platinum, copper, silver, zinc, boron, aluminum, gallium, indium, germanium, tin, lead, phosphorus, bismuth and alkaline earth metals; and a, b, c, d and n are, respectively, the atomic ratios of vanadium, niobium, X, Z and oxygen, relative to molybdenum, wherein:

$0.1 \leq a \leq 1.0$;

$0.01 \leq b \leq 1.0$;

$0.01 \leq c \leq 1.0$;

$0 \leq d \leq 0.1$; and n is a number determined by and consistent with the valence requirements of the other elements present in the compound oxide of formula (1).

3. The catalyst according to item 2 above, wherein X in formula (1) is tellurium.

4. The catalyst according to item 2 or 3 above, wherein Z in formula (1) is at least one element selected from the group consisting of ytterbium, dysprosium and erbium.

5. The catalyst according to item 1 or 2 above, which has an alkali metal content of 0.007 or less in terms of the atomic ratio of an alkali metal, relative to molybdenum.

6. The catalyst according to item 2 above, which is produced by a method comprising:

providing an aqueous mixture of a silica sol and compounds of molybdenum, vanadium, niobium, at least one element selected from the group consisting of tellurium and antimony, and optionally at least one element selected from the group consisting of ytterbium, dysprosium, erbium, cerium, neodymium, samarium, lanthanum, praseodymium, europium, gadolinium, terbium, holmium, thulium, lutetium, scandium, tungsten, chromium, tantalum, titanium, zirconium, hafnium, manganese, rhenium, iron, ruthenium, cobalt, rhodium, nickel, palladium, platinum, copper, silver, zinc, boron, aluminum, gallium, indium, germanium, tin, lead, phosphorus, bismuth and alkaline earth metals;

drying the aqueous mixture, to thereby obtain a catalyst precursor; and calcining the catalyst precursor in an atmosphere of inert gas which is substantially free of molecular oxygen.

7. The catalyst according to item 6 above, wherein the silica sol has an alkali metal content of 0.007 or less in terms of the atomic ratio of an alkali metal, relative to silicon.

8. The catalyst according to item 6 or 7 above, wherein the niobium compound is in the form of a niobium-containing aqueous solution comprising water having dissolved therein a dicarboxylic acid and a niobium compound, wherein the molar ratio of the dicarboxylic acid to niobium is in the range of from 2 to 4.

9. A process for producing acrylonitrile or methacrylonitrile, which comprises reacting propane or isobutane with ammonia and molecular oxygen in the gaseous phase in the presence of an ammoxidation catalyst comprising a compound oxide and a silica carrier having supported thereon the compound oxide, the compound oxide comprising molybdenum (Mo), vanadium (V), niobium (Nb) and at least one element selected from the group consisting of tellurium and antimony, wherein the catalyst has an alkali metal content of 0.01 or less in terms of the atomic ratio of an alkali metal, relative to molybdenum.

10. The process according to item 9 above, wherein, in the catalyst, the silica carrier is present in an amount of from 25 to 70% by weight in terms of $SiO_2$, based on the total weight of the compound oxide and the silica carrier, and the compound oxide is represented by the following formula (1):

$$Mo_{1.0}V_aNb_bX_cZ_dO_n \qquad (1)$$

wherein:

X is at least one element selected from the group consisting of tellurium and antimony;

Z is at least one element selected from the group consisting of ytterbium, dysprosium, erbium, cerium, neodymium, samarium, lanthanum, praseodymium, europium, gadolinium, terbium, holmium, thulium, lutetium, scandium, tungsten, chromium, tantalum, titanium, zirconium, hafnium, manganese, rhenium, iron, ruthenium, cobalt, rhodium, nickel, palladium, platinum, copper, silver, zinc, boron, aluminum, gallium, indium, germanium, tin, lead, phosphorus, bismuth and alkaline earth metals; and a, b, c, d and n are, respectively, the atomic ratios of vanadium, niobium, X, Z and oxygen, relative to molybdenum, wherein:

$0.1 \leq a \leq 1.0$;

$0.01 \leq b \leq 1.0$;

$0.01 \leq c \leq 1.0$;

$0 \leq d \leq 0.1$; and n is a number determined by and consistent with the valence requirements of the other elements present in the compound oxide of formula (1).

11. The process according to item 10 above, wherein X in formula (1) is tellurium.

12. The process according to item 10 or 11 above, wherein Z in formula (1) is at least one element selected from the group consisting of ytterbium, dysprosium and erbium.

13. The process according to item 9 or 10 above, wherein the catalyst has an alkali metal content of 0.007 or less in terms of the atomic ratio of an alkali metal, relative to molybdenum.

14. The process according to item 10 above, wherein the catalyst is produced by a method comprising:

providing an aqueous mixture of a silica sol and compounds of molybdenum, vanadium, niobium, at least one element selected from the group consisting of tellurium and antimony, and optionally at least one element selected from the group consisting of ytterbium, dysprosium, erbium, cerium, neodymium, samarium, lanthanum, praseodymium, europium, gadolinium, terbium, holmium, thulium, lutetium, scandium, tungsten, chromium, tantalum, titanium, zirconium, hafnium, manganese, rhenium, iron, ruthenium, cobalt, rhodium, nickel, palladium, platinum, copper, silver, zinc, boron, aluminum, gallium, indium, germanium, tin, lead, phosphorus, bismuth and alkaline earth metals;

drying the aqueous mixture, to thereby obtain a catalyst precursor; and calcining the catalyst precursor in an atmosphere of inert gas which is substantially free of molecular oxygen.

15. The process according to item 14 above, wherein the silica sol has an alkali metal content of 0.007 or less in terms of the atomic ratio of an alkali metal, relative to silicon.

16. The process according to item 14 or 15 above, wherein the niobium compound is in the form of a niobium-containing aqueous solution comprising water having dissolved therein a dicarboxylic acid and a niobium compound, wherein the molar ratio of the dicarboxylic acid to niobium is in the range of from 2 to 4.

Hereinbelow, the present invention will be described in more detail.

As mentioned above, with respect to the conventional ammoxidation catalysts which comprise a compound oxide and a silica carrier (which provides an attrition resistance) having supported thereon the compound oxide, wherein the compound oxide comprises molybdenum, vanadium, niobium and at least one element selected from the group consisting of tellurium and antimony, there has been a problem in that, when the silica carrier is employed in an amount necessary for imparting a satisfactory attrition resistance to the catalyst, the yield of the desired unsaturated nitrile is likely to be low. For solving the above problem, the present inventors have conducted extensive and intensive studies. As a result, they have unexpectedly found that, by the use of the ammoxidation catalyst of the present invention in which the alkali metal content is extremely small or substantially zero, acrylonitrile or methacrylonitrile can be produced in high yield, as compared to the yield achieved by conventional ammoxidation catalysts containing a silica carrier.

Conventionally, a number of oxide catalysts containing an alkali metal have been known. For example, each of Unexamined Japanese Patent Application Laid-Open Specification Nos. 10-28862, 8-141401 and 5-213848, U.S. Pat. Nos. 4,760,159 and 4,797,381 and EP 0 767 164 A1 describes that an alkali metal is used as a component element for an oxide catalyst for use in the ammoxidation of an alkane, wherein the catalyst also contains molybdenum, vanadium, niobium and at least one element selected from the group consisting of tellurium and antimony. However, in each of these prior art documents, there is no teaching or suggestion that, for improving the yield of an unsaturated nitrile, it is effective to reduce the alkali metal content of a catalyst to a level as low as possible. Further, these conventional oxide catalysts are disadvantageous in that, in the ammoxidation of an alkane, a satisfactorily high yield of the desired unsaturated nitrile cannot be achieved.

The present inventors have for the first time found that, with respect to an ammoxidation catalyst for use in producing acrylonitrile or methacrylonitrile from propane or isobutane by ammoxidation in the gaseous phase, which comprises a silica carrier having supported thereon a compound oxide of molybdenum, vanadium, niobium and at least one element selected from the group consisting of tellurium and antimony, by reducing the alkali metal content of the catalyst to a level as low as possible, the yield of acrylonitrile or methacrylonitrile can be improved.

The ammoxidation catalyst of the present invention comprises a compound oxide and a silica carrier having supported thereon the compound oxide, wherein the compound oxide comprises molybdenum (Mo), vanadium (V), niobium (Nb) and at least one element selected from the group consisting of tellurium and antimony. The most essential feature of the ammoxidation catalyst of the present invention resides in that the catalyst has an alkali metal content of 0.01 or less in terms of the atomic ratio of an alkali metal, relative to molybdenum.

In the ammoxidation catalyst of the present invention, it is required that the compound oxide be supported on a silica carrier. The silica carrier provides an attrition resistance, which is required to be high, especially when the ammoxidation catalyst is used in a fluidized-bed reactor. In the ammoxidation catalyst of the present invention, it is preferred that the amount of the silica carrier is from 25 to 70% by weight in terms of SiO$_2$, more advantageously from 30 to 50% by weight in terms of SiO$_2$, based on the total weight of the compound oxide and the silica carrier.

In the ammoxidation catalyst of the present invention, it is preferred that the compound oxide is represented by the following formula (1):

$$Mo_{1.0}V_aNb_bX_cZ_dO_n \qquad (1)$$

wherein:

X is at least one element selected from the group consisting of tellurium and antimony;

Z is at least one element selected from the group consisting of ytterbium, dysprosium, erbium, cerium, neodymium, samarium, lanthanum, praseodymium, europium, gadolinium, terbium, holmium, thulium, lutetium, scandium, tungsten, chromium, tantalum, titanium, zirconium, hafnium, manganese, rhenium, iron, ruthenium, cobalt, rhodium, nickel, palladium, platinum, copper, silver, zinc, boron, aluminum, gallium, indium, germanium, tin, lead, phosphorus, bismuth and alkaline earth metals; and a, b, c, d and n are, respectively, the atomic ratios of vanadium, niobium, X, Z and oxygen, relative to molybdenum, wherein:

$0.1 \leq a \leq 1.0$;

preferably $0.2 \leq a \leq 0.5$;

$0.01 \leq b \leq 1.0$;

preferably $0.01 \leq b \leq 0.5$;

$0.01 \leq c \leq 1.0$;

preferably $0.1 \leq c \leq 0.5$;

$0 \leq d \leq 0.1$;

preferably $0.005 \leq d \leq 0.05$; and n is a number determined by and consistent with the valence requirements of the other elements present in the compound oxide of formula (1).

Further, it is more preferred that X in formula (1) is tellurium. It is also more preferred that Z in formula (1) is at least one element selected from the group consisting of ytterbium, dysprosium, erbium, cerium, neodymium, samarium, lanthanum, praseodymium, europium, gadolinium, terbium, holmium, thulium, lutetium and scandium, more advantageously at least one element selected from the group consisting of ytterbium, dysprosium and erbium, still more advantageously ytterbium.

In the present invention, it is requisite that the alkali metal content of the ammoxidation catalyst be 0.01 or less, preferably 0.007 or less, more preferably 0.005 or less, most preferably 0, in terms of the atomic ratio of an alkali metal, relative to molybdenum.

Representative examples of sources of component elements for the compound oxide of the ammoxidation catalyst of the present invention include ammonium heptamolybdate [(NH$_4$)$_6$Mo$_7$O$_{24}$·4H$_2$O] as a source of molybdenum; ammonium metavanadate (NH$_4$VO$_3$) as a source of vanadium; a niobic acid, an inorganic acid salt of niobium or an organic acid salt of niobium as a source of niobium; telluric acid (H$_6$TeO$_6$) as a source of tellurium; and diantimony trioxide (Sb$_2$O$_3$) as a source of antimony. Further, a representative example of a source of a silica carrier is a silica sol.

With respect to the source of niobium, it is preferred to use a niobic acid. The "niobic acid" is a hydrated compound represented by the following formula: Nb$_2$O$_5$.nH$_2$O, which is also known as "niobium hydroxide" or "niobium oxide hydrate". It is especially preferred to use a niobium-containing aqueous solution disclosed in EP 0 895 809 A1, which comprises water having dissolved therein a dicarboxylic acid, a niobium compound and optionally ammonia, wherein the molar ratio of the dicarboxylic acid to niobium is 1 to 4 and the molar ratio of the ammonia to niobium is 0 to 2. In the niobium-containing aqueous solution, it is preferred that the molar ratio of the dicarboxylic acid to niobium is in the range of from 2 to 4, more advantageously from 2 to 3.5. In addition, as a dicarboxylic acid, preferred is oxalic acid.

Examples of sources of component element Z (i.e., ytterbium, dysprosium, erbium, cerium, neodymium, samarium, lanthanum, praseodymium, europium, gadolinium, terbium, holmium, thulium, lutetium, scandium, tungsten, chromium, tantalum, titanium, zirconium, hafnium, manganese, rhenium, iron, ruthenium, cobalt, rhodium, nickel, palladium, platinum, copper, silver, zinc, boron, aluminum, gallium, indium, germanium, tin, lead, phosphorus, bismuth and/or alkaline earth metals) include organic acid salts, nitrates, chlorides, hydroxides and oxides of the elements.

By a catalyst production method in which, as sources of component elements for the compound oxide and a source of the silica carrier, use is made of those sources containing an extremely small amount of an alkali metal or substantially no alkali metal, there can be produced the ammoxidation catalyst of the present invention in which the alkali metal content is extremely small or substantially zero.

A silica sol generally contains a large amount of an alkali metal, for example, sodium (Na). When a silica sol containing a large amount of an alkali metal is used as a source of a silica carrier in the production of a catalyst (in which the silica carrier is employed in an amount necessary for imparting a satisfactorily high attrition resistance to the catalyst), the catalyst inevitably contains a large amount of the alkali metal derived from the silica sol. Therefore, for obtaining the ammoxidation catalyst of the present invention in which the alkali metal content is extremely small or substantially zero, it is preferred that the silica sol has an alkali metal content of 0.007 or less, more advantageously 0.003 or less, further more advantageously 0.0005 or less, most advantageously 0, in terms of the atomic ratio of an alkali metal, relative to silicon.

Methods for preparing a high purity silica sol having a small alkali metal content are disclosed in, for example, U.S. Pat. No. 4,624,800, EP 0 464 289 B1 (corresponding to Unexamined Japanese Patent Application Laid-Open Specification No. 4-231319) and Unexamined Japanese Patent Application Laid-Open Specification No. 6-316407.

The ammoxidation catalyst of the present invention can be produced by a conventional method. For example, the catalyst can be produced by a method comprising the steps of (1) preparing an aqueous mixture of raw materials (for example, a slurry of raw materials), (2) drying the aqueous mixture of raw materials obtained in step (1) above to obtain a dried catalyst precursor, and (3) subjecting the dried catalyst precursor obtained in step (2) above to calcination.

Hereinbelow, explanation is made with respect to a preferred embodiment of the above-mentioned method for producing the ammoxidation catalyst of the present invention, which comprises steps (1), (2) and (3) above.

In step (1), an aqueous mixture of raw materials is prepared.

First, an aqueous mixture is prepared by dissolving ammonium heptamolybdate, ammonium metavanadate and telluric acid in water (this aqueous mixture is designated "aqueous mixture A").

Alternatively, when antimony is used as a component element, an aqueous mixture is first prepared by a method in which a diantimony trioxide powder is dispersed in an aqueous solution of ammonium metavanadate to thereby obtain a dispersion, and the obtained dispersion is heated under reflux conditions to obtain a solution or slurry, and then, ammonium heptamolybdate and optionally telluric acid are added to the obtained solution or slurry to obtain an aqueous mixture (this aqueous mixture is designated "aqueous mixture A'").

On the other hand, oxalic acid and a niobic acid are dissolved in water while heating and stirring, to thereby obtain an aqueous mixture (this aqueous mixture is designated "aqueous mixture B").

When use is made of optional component element Z (i.e., at least one element selected from the group consisting of ytterbium, dysprosium, erbium, cerium, neodymium, samarium, lanthanum, praseodymium, europium, gadolinium, terbium, holmium, thulium, lutetium, scandium, tungsten, chromium, tantalum, titanium, zirconium, hafnium, manganese, rhenium, iron, ruthenium, cobalt, rhodium, nickel, palladium, platinum, copper, silver, zinc, boron, aluminum, gallium, indium, germanium, tin, lead, phosphorus, bismuth and alkaline earth metals), a nitrate, an oxalate, an acetate, a hydroxide, an oxide, an ammonium salt, a carbonate or the like of optional component element Z is dissolved in water to obtain an aqueous mixture (this aqueous mixture is designated "aqueous mixture C"). When ytterbium is used as optional component element Z, it is preferred to use ytterbium nitrate.

To aqueous mixture A or A' are added aqueous mixture B, a silica sol and optionally aqueous mixture C, to thereby obtain an aqueous mixture of raw materials.

The addition of a silica sol can be made at any time during the above preparation operation for the aqueous mixture of raw materials, which comprises preparing aqueous mixture A or A', aqueous mixture B and optionally aqueous mixture C, and mixing together these aqueous mixture A or A', aqueous mixture B and optionally aqueous mixture C.

The aqueous mixture of raw materials may be obtained in the form of either a solution or a slurry. However, the aqueous mixture of raw materials is generally obtained in the form of a slurry.

In step (2), the aqueous mixture of raw materials obtained in step (1) above is subjected to spray drying. The spray drying of the aqueous mixture of raw materials can be generally conducted by centrifugation, two-phase flow nozzle method or high pressure nozzle method to obtain a dried particulate catalyst precursor. n this instance, it is preferred to use air which has been heated by steam, an electric heater or the like, as a heat source for drying. It is preferred that the temperature of the spray dryer at an entrance to the dryer section thereof is from 150 to 300° C.

In step (3), the dried particulate catalyst precursor obtained in step (2) above is calcined to thereby obtain a catalyst. The dried particulate catalyst precursor is calcined in an atmosphere of an inert gas, such as nitrogen gas, argon gas or helium gas, which is substantially free of oxygen, preferably under a flow of an inert gas, at a temperature of 500 to 700° C., preferably 550 to 650° C., for 0.5 to 20 hours, preferably 1 to 8 hours.

For the calcination, use can be made of a kiln, such as a rotary kiln, a tunnel kiln, a muffle kiln and a fluidized firing kiln.

Prior to the calcination in step (3), the dried catalyst precursor may be subjected to pre-calcination. That is, prior to the calcination in step (3), the dried catalyst precursor obtained in step (2) above may be pre-calcined in an atmosphere of air or under a flow of air at 200 to 400° C. for 1 to 5 hours.

Acrylonitrile or methacrylonitrile can be produced by reacting propane or isobutane with ammonia and molecular oxygen in the gaseous phase in the presence of the catalyst of the present invention.

Accordingly, as mentioned above, in another aspect of the present invention, there is provided a process for producing acrylonitrile or methacrylonitrile, which comprises reacting propane or isobutane with ammonia and molecular oxygen in the gaseous phase in the presence of the ammoxidation catalyst defined above.

Propane or isobutane and ammonia used in the process of the present invention need not be of a very high purity but may be of a commercial grade.

Examples of sources of molecular oxygen include air, oxygen-rich air, and pure oxygen. Further, such a source of molecular oxygen may be diluted with helium, neon, argon, nitrogen, carbon dioxide, steam or the like.

In the process of the present invention, the molar ratio of ammonia to propane or isobutane used for the ammoxidation may be generally in the range of from 0.3 to 1.5, preferably from 0.8 to 1.2.

The molar ratio of molecular oxygen to propane or isobutane used for the ammoxidation may be generally in the range of from 0.1 to 6, preferably from 0.1 to 4.

In the process of the present invention, the ammoxidation temperature is generally in the range of from 350 to 500° C., preferably from 380 to 470° C.

In the process of the present invention, the ammoxidation pressure is generally in the range of from 0.5 to 5 atm., preferably from atmospheric pressure to 3 atm.

The time of contact (contact time) between the gaseous feedstocks and the catalyst is generally in the range of from 0.1 to 10 sec-g/cc, preferably from 0.5 to 5 sec.g/cc. In the process of the present invention, the contact time during the ammoxidation of propane or isobutane is determined according to the following formula:

$$\text{Contact time (sec} \cdot \text{g/cc)} = (W/F) \times \frac{273}{(273+T)}$$

wherein:
W represents the weight (g) of the catalyst contained in the reactor;
F represents the flow rate (Ncc/sec) of the gaseous feedstocks [Ncc means cc as measured under the normal temperature and pressure conditions (0° C., 1 atm)]; and
T represents the ammoxidation temperature (° C.).

The process of the present invention for producing acrylonitrile or methacrylonitrile by ammoxidation of propane or isobutane in the gaseous phase can be conducted in a conventional reactor, such as a fixed-bed reactor, a fluidized-bed reactor or a moving-bed reactor. However, most preferred is a fluidized-bed reactor; the reason for this resides in that, when a fluidized-bed reactor is used, the removal of reaction heat generated during the ammoxidation can be easily effected, so that the temperature of the catalyst bed can be maintained uniform, and the withdrawal and addition of a catalyst can be easily effected during the ammoxidation.

BEST MODE FOR CARRYING OUT THE INVENTION

Hereinbelow, the present invention will be described in more detail with reference to the following Reference Example, Examples and Comparative Examples, which are for illustrative purposes only, and should not be construed as limiting the scope of the present invention.

In the following Examples and Comparative Examples, the conversion (%) of propane, the selectivity (%) for acrylonitrile, and the yield (%) of acrylonitrile, each used for evaluating the results of the ammoxidation of propane, are defined as follows:

$$\text{Conversion (\%) of propane} = \frac{\text{(mole of propane reacted)}}{\text{(mole of propane fed)}} \times 100$$

$$\text{Selectivity (\%) for acrylonitrile} = \frac{\text{(mole of acrylonitrile formed)}}{\text{(mole of propane reacted)}} \times 100$$

$$\text{Yield (\%) of acrylonitrile} = \frac{\text{(mole of acrylonitrile formed)}}{\text{(mole of propane fed)}} \times 100$$

REFERENCE EXAMPLE (Preparation of a silica sol)

As a starting material for producing a silica sol, there was used a water glass having an $SiO_2$ content of 28.5% by weight and an $Na_2O$ content of 9.5% by weight. 10.0 kg of the water glass was dissolved in 30.0 kg of water, to thereby obtain a diluted aqueous solution of sodium silicate having a sodium silicate content of 7.13% by weight in terms of $SiO_2$.

The diluted aqueous solution of sodium silicate was cooled to about 7° C., and then, passed through a hydrogen-type strongly acidic cation exchange resin at a flow rate of 0.15 liter/min per liter of the cation exchange resin so as to replace alkali metal ions in the diluted sodium silicate solution by hydrogen ions, to thereby obtain 34 kg of a silicic acid-containing aqueous liquid.

The silicic acid-containing aqueous liquid was diluted with water so that the silicic acid content of the aqueous liquid became 5.0% by weight in terms of $SiO_2$, and then, the resultant diluted aqueous liquid was cooled to about 7° C.

To the diluted aqueous liquid was added 16.8 g of oxalic acid ($H_2C_2O_4.2H_2O$) and then added 483 g of concentrated sulfuric acid ($H_2SO_4$ content: 95%), followed by stirring at about 7° C. for 2 hours.

The resultant mixture was continuously subjected to a sequence of treatments with anion and cation exchangers, in which the mixture was passed through a hydroxide-type strongly basic anion exchange resin at a flow rate of 0.15 liter/min per liter of the anion exchange resin, which was used in a sufficient amount to have hydroxide ions in large excess of the negatively charged spieces in the mixture so as to replace the negatively charged spieces in the mixture by hydroxide ions, and then the resultant anion exchange treated mixture was immediately passed through a hydrogen-type strongly acidic cation exchange resin at a flow rate of 0.15 liter/min per liter of the cation exchange resin, which was used in a sufficient amount to have hydrogen ions in large excess of the positively charged spieces in the mixture so as to replace the positively charged spieces in the mixture by hydrogen ions, to thereby obtain a silicic acid-containing aqueous liquid having a low metal content (hereinafter referred to simply as "low metal content silicic acid-containing liquid"). During the above sequence of treatments, the initial 4.1 kg portion of the low metal content silicic acid-containing liquid was added to a mixture of 35 g of 25 % aqueous ammonia and 1,100 g of water to obtain an aqueous mixture.

The aqueous mixture was charged into a stainless steel (SUS according to Japanese industrial standards) reactor equipped with a condenser and heated to about 97° C. over about 45 minutes while carefully controlling the temperature of the mixture in the reactor so as not to cause the mixture to boil.

Then, about 37 kg of the low metal content silicic acid-containing liquid, which was obtained by further conducting the above sequence of treatments after harvesting the above 4.1 kg portion of the liquid, was charged into the above SUS reactor over about 5 hours while stirring. During the addition of the low metal content silicic acid-containing liquid into the SUS reactor over the about 5 hours, the pH value of the contents of the SUS reactor was maintained at about 9 to 10 by adding an aqueous ammonia to the SUS reactor, and the temperature of the contents of the SUS reactor was maintained at about 96 to 99° C. It should be noted that the low metal content silicic acid-containing liquid is unstable. Therefore, the low metal content silicic acid-containing liquid was put to use as immediately as possible after the above-mentioned sequence of anion and cation exchangers treatments. After completion of the addition of the low metal content silicic acid-containing liquid into the SUS reactor, the resultant mixture was further stirred at about 97° C. for 1 hour, to thereby obtain a preliminary silica sol.

The preliminary silica sol was concentrated by means of an ultrafiltration membrane, to thereby obtain a silica sol having an $SiO_2$ content of 30% by weight.

The above-described procedure for the preparation of a silica sol was conducted substantially in accordance with the method disclosed in Unexamined Japanese Patent Application Laid-Open Specification No. 4-231319 (corresponding to EP 0 464 289 B1).

The above-described procedure for the preparation of a silica sol was repeated three times to obtain three batches of silica sol, and the obtained batches were pooled. The pooled silica sol was designated "silica sol S-1".

The alkali metal content of silica sol S-1 in terms of the atomic ratio of an alkali metal, relative to silicon, was determined by the following method.

1.000 g of silica sol S-1 was accurately taken and dissolved in a mixture of 5 ml of aqua regia and 1 ml of 49 wt % hydrofluoric acid while heating, and then, the resultant solution was diluted to 100 ml with water, to thereby obtain a sample solution. Aliquots of the obtained sample solution were individually, appropriately diluted with water, and the resultant solutions were individually subjected to a measurement by means of a flameless atomic absorption spectrometer (Z-8270, manufactured and sold by Hitachi Ltd., Japan), thereby quantitatively determining the amounts of sodium (Na) and potassium (K). Additionally, aliquots of the above sample solution were individually, appropriately diluted with water, and the resultant solutions wre individually subjected to a measurement by means of an inductively coupled plasma-mass spectrometer (ICP-MS) (Model PQΩ, manufactured and sold by VG Elemental, England), thereby quantitatively determining the amounts of alkali metal elements other than Na and K. Based on the obtained amounts of the alkali metal elements contained in the sample solution, a calculation was made, to thereby determine the alkali metal content of silica sol S-1 in terms of the atomic ratio of an alkali metal, relative to silicon.

As a result, it was found that the alkali metal content of silica sol S-1 was 0.00007 in terms of the atomic ratio of an alkali metal, relative to silicon.

EXAMPLE 1

(Preparation of an ammoxidation catalyst)

An ammoxidation catalyst, which comprises a compound oxide and a silica carrier having supported thereon the compound oxide, wherein the silica carrier is present in an amount of 30% by weight in terms of $SiO_2$, based on the total weight of the compound oxide and the silica carrier, and wherein the compound oxide is represented by the formula:

$$Mo_{1.0}V_{0.32}Nb_{0.12}Te_{0.22}O_n,$$

wherein n is a number determined by and consistent with the valence requirements of the other elements present in the compound oxide of the above formula, which applies to n appearing in the formulae representing the compound oxides obtained in all of the subsequent Examples, was prepared as follows.

543.4 g of ammonium heptamolybdate [$(NH_4)_6Mo_7O_{24}\cdot 4H_2O$], 115.2 g of ammonium metavanadate ($NH_4VO_3$) and 156.1 g of telluric acid ($H_6TeO_6$) were added to 2,300 g of water, and the resultant mixture was heated to about 60° C. while stirring, to obtain a solution, and the obtained solution was cooled to about 30° C., to thereby obtain aqueous mixture A-1.

64.0 g of a niobic acid ($Nb_2O_5\cdot nH_2O$) ($Nb_2O_5$ content: 76.6% by weight) and 139.5 g of oxalic acid ($H_2C_2O_4\cdot 2H_2O$) were added to 530 g of water, and the resultant mixture was heated to about 60° C. while stirring, followed by cooling to about 30° C., to thereby obtain aqueous mixture B-1. In the obtained aqueous mixture B-1, the molar ratio of oxalic acid to niobium (hereinafter, frequently referred to as "[$H_2C_2O_4$:Nb] molar ratio") was 3.0.

To aqueous mixture A-1 was added aqueous mixture B-1 and then added 1,000 g of silica sol S-1 while stirring, to thereby obtain an aqueous mixture of raw materials.

The obtained aqueous mixture of raw materials was subjected to spray drying using a centrifugation type spray-drying apparatus under conditions wherein the inlet and outlet temperatures of the apparatus were 240° C. and 145° C., respectively, to thereby obtain a dried, spherical particulate catalyst precursor.

The catalyst precursor was pre-calcined at 275° C. for 2 hours in an atmosphere of air to obtain an oxide. 85 g of the oxide was charged into a stainless steel (SUS) tube having an inner diameter of 1 inch, and then calcined at 600° C. for 2 hours under a stream of nitrogen gas at a flow rate of 150 Ncc/min, to thereby obtain a catalyst.

The alkali metal content of the obtained catalyst in terms of the atomic ratio of an alkali metal, relative to molybdenum, was determined as follows.

0.300 g of the catalyst was accurately taken and dissolved in a mixture of 5 ml of aqua regia and 1 ml of 49 wt % hydrofluoric acid while heating, and then, 10 the resultant solution was diluted to 100 ml with water, to thereby obtain a sample solution. Aliquots of the sample solution were individually, appropriately diluted with water, and the resultant solutions were individually subjected to a measurement by means of a flameless atomic absorption spectrometer (Z-8270, manufactured and sold by Hitachi Ltd., Japan), thereby quantitatively determining the amounts of sodium (Na) and potassium (K). Additionally, aliquots of the above sample solution were individually, appropriately diluted with water, and the resultant solutions were individually subjected to a measurement by means of an inductively coupled plasma-mass spectrometer (ICP-MS) (Model PQΩ, manufactured and sold by VG Elemental, England), thereby quantitatively determining the amounts of alkali metal elements other than Na and K and molybdenum. Based on the obtained amounts of the elements contained in the sample solution, a calculation was made, to thereby determine the alkali metal content of the catalyst in terms of the atomic ratio of an alkali metal, relative to molybdenum.

As a result, it was found that the alkali metal content of the catalyst was 0.0007 in terms of the atomic ratio of an alkali metal, relative to molybdenum.

(Ammoxidation of propane)

Using the catalyst obtained above, an ammoxidation of propane was performed as follows.

45 g of the obtained catalyst was charged into a Vycor glass fluidized-bed reaction tube having an inner diameter of 25 mm. In the reaction tube containing the catalyst, an ammoxidation of propane was performed under conditions wherein the contact time between the catalyst and a gaseous feedstock mixture (i.e., a gaseous mixture of propane, ammonia, molecular oxygen and helium) was 3.0 sec·g/cc, the [propane:ammonia:molecular oxygen:helium] molar ratio in the gaseous feedstock mixture was 1.0:1.2:3.0:12.0, the temperature was 430° C. and the pressure was atmospheric.

The results of the above ammoxidation are shown in Table 1.

EXAMPLE 2

(Preparation of an ammoxidation catalyst)

An ammoxidation catalyst, which comprises a compound oxide and a silica carrier having supported thereon the compound oxide, wherein the silica carrier is present in an amount of 30% by weight in terms of $SiO_2$, based on the total weight of the compound oxide and the silica carrier, and wherein the compound oxide is represented by the formula:

$$Mo_{1.0}V_{0.32}Nb_{0.12}Te_{0.22}O_n,$$

was prepared as follows.

543.4 g of ammonium heptamolybdate [$(NH_4)_6Mo_7O_{24}\cdot 4H_2O$], 115.2 g of ammonium metavanadate ($NH_4VO_3$) and 156.1 g of telluric acid ($H_6TeO_6$) were added to 2,300 g of water, and the resultant mixture was heated to about 60° C. while stirring, to obtain a solution, and the obtained solution was cooled to about 30° C., to thereby obtain aqueous mixture A-2.

64.0 g of a niobic acid ($Nb_2O_5\cdot nH_2O$) ($Nb_2O_5$ content: 76.6% by weight) and 139.5 g of oxalic acid ($H_2C_2O_4\cdot 2H_2O$) were added to 530 g of water, and the resultant mixture was heated to about 60° C. while stirring, followed by cooling to about 30° C., to thereby obtain aqueous mixture B-2. In the obtained aqueous mixture B-2, the [$H_2C_2O_4$:Nb] molar ratio was 3.0.

To aqueous mixture A-2 were added, while stirring, aqueous mixture B-2, an aqueous sodium nitrate solution composed of 10 g of water and 1.09 g of sodium nitrate ($NaNO_3$), and 1,000 g of silica sol S-1 prepared in Reference Example, to thereby obtain an aqueous mixture of raw materials.

The aqueous mixture of raw materials was subjected to spray drying using a centrifugation type spray-drying apparatus under conditions wherein the inlet and outlet temperatures of the apparatus were 240° C. and 145° C., respectively, to thereby obtain a dried, spherical particulate catalyst precursor.

The obtained catalyst precursor was pre-calcined at 275° C. for 2 hours in an atmosphere of air to obtain an oxide. 85 g of the obtained oxide was charged into a stainless steel (SUS) tube having an inner diameter of 1 inch, and then calcined at 600° C. for 2 hours under a stream of nitrogen gas at a flow rate of 150 Ncc/min, to thereby obtain a catalyst.

The alkali metal content of the obtained catalyst was determined by the same method as in Example 1. It was found that the alkali metal content of the catalyst was 0.0048 in terms of the atomic ratio of an alkali metal, relative to molybdenum.

(Ammoxidation of propane)

An ammoxidation was performed in the presence of the obtained catalyst under the same conditions as in Example 1. The results of the ammoxidation are shown in Table 1.

EXAMPLE 3

(Preparation of an ammoxidation catalyst)

An ammoxidation catalyst, which comprises a compound oxide and a silica carrier having supported thereon the compound oxide, wherein the silica carrier is present in an amount of 30% by weight in terms of $SiO_2$, based on the total weight of the compound oxide and the silica carrier, and wherein the compound oxide is represented by the formula:

$$Mo_{1.0}V_{0.32}Nb_{0.12}Te_{0.22}O_n,$$

was prepared in substantially the same manner as in Example 2, except that use was made of 1.65 g of sodium nitrate instead of 1.09 g of sodium nitrate.

The alkali metal content of the obtained catalyst was determined by the same method as in Example 1. It was found that the alkali metal content of the catalyst was 0.0069 in terms of the atomic ratio of an alkali metal, relative to molybdenum.

(Ammoxidation of propane)

An ammoxidation was performed in the presence of the obtained catalyst under the same conditions as in Example 1. The results of the ammoxidation are shown in Table 1.

COMPARATIVE EXAMPLE 1

(Preparation of an ammoxidation catalyst)

An ammoxidation catalyst, which comprises a compound oxide and a silica carrier having supported thereon the compound oxide, wherein the silica carrier is present in an amount of 30% by weight in terms of $SiO_2$, based on the total weight of the compound oxide and the silica carrier, and wherein the compound oxide is represented by the formula:

$$Mo_{1.0}V_{0.32}Nb_{0.12}Te_{0.22}O_n,$$

was prepared in substantially the same manner as in Example 2, except that use was made of an aqueous sodium nitrate solution composed of 30 g of water and 3.12 g of sodium nitrate, instead of an aqueous sodium nitrate solution composed of 10 g of water and 1.09 g of sodium nitrate.

The alkali metal content of the obtained catalyst was determined by the same method as in Example 1. It was found that the alkali metal content of the catalyst was 0.0125 in terms of the atomic ratio of an alkali metal, relative to molybdenum.

(Ammoxidation of propane) An ammoxidation was performed in the presence of the obtained catalyst under the same conditions as in Example 1. The results of the ammoxidation are shown in Table 1.

COMPARATIVE EXAMPLE 2

(Preparation of an ammoxidation catalyst)

An ammoxidation catalyst, which comprises a compound oxide and a silica carrier having supported thereon the compound oxide, wherein the silica carrier is present in an amount of 30% by weight in terms of $SiO_2$, based on the total weight of the compound oxide and the silica carrier, and wherein the compound oxide is represented by the formula:

$$Mo_{1.0}V_{0.32}Nb_{0.12}Te_{0.22}O_n,$$

was prepared in substantially the same manner as in Comparative Example 1, except that use was made of 6.77 g of sodium nitrate instead of 3.12 g of sodium nitrate.

The alkali metal content of the obtained catalyst was determined by the same method as in Example 1. It was found that the alkali metal content of the catalyst was 0.0263 in terms of the atomic ratio of an alkali metal, relative to molybdenum.

(Ammoxidation of propane)

An ammoxidation was performed in the presence of the obtained catalyst under the same conditions as in Example 1. The results of the ammoxidation are shown in Table 1.

COMPARATIVE EXAMPLE 3

(Preparation of an ammoxidation catalyst)

An ammoxidation catalyst, which comprises a compound oxide and a silica carrier having supported thereon the compound oxide, wherein the silica carrier is present in an amount of 30% by weight in terms of $SiO_2$, based on the total weight of the compound oxide and the silica carrier, and wherein the compound oxide is represented by the formula:

$$Mo_{1.0}V_{0.32}Nb_{0.12}Te_{0.22}O_n,$$

was prepared in substantially the same manner as in Comparative Example 1, except that use was made of 8.11 g of potassium nitrate ($KNO_3$) instead of 3.12 g of sodium nitrate.

The alkali metal content of the obtained catalyst was determined by the same method as in Example 1. It was found that the alkali metal content of the catalyst was 0.0265 in terms of the atomic ratio of an alkali metal, relative to molybdenum.

(Ammoxidation of propane)

An ammoxidation was performed in the presence of the obtained catalyst under the same conditions as in Example 1. The results of the ammoxidation are shown in Table 1.

EXAMPLE 4

(Preparation of an ammoxidation catalyst)

An ammoxidation catalyst, which comprises a compound oxide and a silica carrier having supported thereon the compound oxide, wherein the silica carrier is present in an amount of 30% by weight in terms of $SiO_2$, based on the total weight of the compound oxide and the silica carrier, and wherein the compound oxide is represented by the formula:

$$Mo_{1.0}V_{0.32}Nb_{0.12}Te_{0.22}O_n,$$

was prepared as follows.

543.4 g of ammonium heptamolybdate [$(NH_4)_6Mo_7O_{24} \cdot 4H_2O$], 115.2 g of ammonium metavanadate ($NH_4VO_3$) and 156.1 g of telluric acid ($H_6TeO_6$) were added to 2,300 g of water, and the resultant mixture was heated to about 60° C. while stirring, to obtain a solution, and the obtained solution was cooled to about 30° C., to thereby obtain aqueous mixture A-4.

64.0 g of a niobic acid ($Nb_2O_5 \cdot nH_2O$) ($Nb_2O_5$ content: 76.6% by weight) and 139.5 g of oxalic acid ($H_2C_2O_4 \cdot 2H_2O$) were added to 530 g of water, and the resultant mixture was heated to about 60° C. while stirring, followed by cooling to about 30° C., to thereby obtain aqueous mixture B-4. In the obtained aqueous mixture B-4, the [$H_2C_2O_4$:Nb] molar ratio was 3.0.

To 1,000 g of silica sol S-1 prepared in Reference Example were added an aqueous sodium nitrate solution composed of 10 g of water and 0.15 g of sodium nitrate ($NaNO_3$), to thereby obtain silica sol S-4 having an alkali metal content of 0.00042 in terms of the atomic ratio of an alkali metal, relative to silicon.

To aqueous mixture A-4 was added aqueous mixture B-4 and then added all of silica sol S-4 while stirring, to thereby obtain an aqueous mixture of raw materials.

The aqueous mixture of raw materials was subjected to spray drying using a centrifugation type spray-drying apparatus under conditions wherein the inlet and outlet temperatures of the apparatus were 240° C. and 145° C., respectively, to thereby obtain a dried, spherical particulate catalyst precursor.

The obtained catalyst precursor was pre-calcined at 275° C. for 2 hours in an atmosphere of air to obtain an oxide. 85 g of the obtained oxide was charged into a stainless steel (SUS) tube having an inner diameter of 1 inch, and then calcined at 600° C. for 2 hours under a stream of nitrogen gas at a flow rate of 150 Ncc/min, to thereby obtain a catalyst.

The alkali metal content of the obtained catalyst was determined by the same method as in Example 1. It was found that the alkali metal content of the catalyst was 0.0013 in terms of the atomic ratio of an alkali metal, relative to molybdenum.

(Ammoxidation of propane)

An ammoxidation was performed in the presence of the obtained catalyst under the same conditions as in Example 1. The results of the ammoxidation are shown in Table 1.

EXAMPLE 5

(Preparation of an ammoxidation catalyst)

An ammoxidation catalyst, which comprises a compound oxide and a silica carrier having supported thereon the compound oxide, wherein the silica carrier is present in an amount of 30% by weight in terms of $SiO_2$, based on the total weight of the compound oxide and the silica carrier, and wherein the compound oxide is represented by the formula:

$$Mo_{1.0}V_{0.32}Nb_{0.12}Te_{0.22}O_n,$$

was prepared in substantially the same manner as in Example 4, except that, instead of 0.15 g of sodium nitrate, 1.65 g of sodium nitrate was used, to thereby obtain silica sol S-5 having an alkali metal content of 0.00392 in terms of the atomic ratio of an alkali metal, relative to silicon (silica sol S-5 was used instead of silica sol S-4).

The alkali metal content of the obtained catalyst was determined by the same method as in Example 1. It was found that the alkali metal content of the catalyst was 0.0069 in terms of the atomic ratio of an alkali metal, relative to molybdenum.

(Ammoxidation of propane)

An ammoxidation was performed in the presence of the obtained catalyst under the same conditions as in Example 1. The results of the ammoxidation are shown in Table 1.

COMPARATIVE EXAMPLE 4

(Preparation of an ammoxidation catalyst)

An ammoxidation catalyst, which comprises a compound oxide and a silica carrier having supported thereon the compound oxide, wherein the silica carrier is present in an amount of 30% by weight in terms of $SiO_2$, based on the total weight of the compound oxide and the silica carrier, and wherein the compound oxide is represented by the formula:

$$Mo_{1.0}V_{0.32}Nb_{0.12}Te_{0.22}O_n,$$

was prepared in substantially the same manner as in Example 4, except that, instead of an aqueous sodium nitrate solution composed of 10 g of water and 0.15 g of sodium nitrate, use was made of an aqueous sodium nitrate solution composed of 30 g of water and 6.77 g of sodium nitrate, to obtain a silica sol having an alkali metal content of 0.0159 in terms of the atomic ratio of an alkali metal, relative to silicon (this silica sol was used instead of silica sol S-4).

The alkali metal content of the obtained catalyst was determined by the same method as in Example 1. It was found that the alkali metal content of the catalyst was 0.0264 in terms of the atomic ratio of an alkali metal, relative to molybdenum.

(Ammoxidation of propane)

An ammoxidation was performed in the presence of the obtained catalyst under the same conditions as in Example 1. The results of the ammoxidation are shown in Table 1.

COMPARATIVE EXAMPLE 5

(Preparation of an ammoxidation catalyst)

An ammoxidation catalyst, which comprises a compound oxide and a silica carrier having supported thereon the compound oxide, wherein the silica carrier is present in an amount of 30% by weight in terms of $SiO_2$, based on the total weight of the compound oxide and the silica carrier, and wherein the compound oxide is represented by the formula:

$$Mo_{1.0}V_{0.32}Nb_{0.12}Te_{0.22}O_n,$$

was prepared in substantially the same manner as in Example 1, except that, instead of 1,000 g of silica sol S-1, use was made of 1,500 g of a silica sol (ST-20, manufactured and sold by Nissan Chemical Industries, LTD., Japan) which has an $SiO_2$ content of 20% by weight and an alkali metal content of 0.0155 in terms of the atomic ratio of an alkali metal, relative to silicon.

The alkali metal content of the obtained catalyst was determined by the same method as in Example 1. It was found that the alkali metal content of the catalyst was 0.0266 in terms of the atomic ratio of an alkali metal, relative to molybdenum.

(Ammoxidation of propane)

An ammoxidation was performed in the presence of the obtained catalyst under the same conditions as in Example 1. The results of the ammoxidation are shown in Table 1.

EXAMPLE 6

(Preparation of an ammoxidation catalyst)

An ammoxidation catalyst, which comprises a compound oxide and a silica carrier having supported thereon the compound oxide, wherein the silica carrier is present in an amount of 30% by weight in terms of $SiO_2$, based on the total weight of the compound oxide and the silica carrier, and wherein the compound oxide is represented by the formula:

$$Mo_{1.0}V_{0.32}Nb_{0.12}Te_{0.22}Yb_{0.02}O_n,$$

was prepared as follows.

534.1 g of ammonium heptamolybdate [$(NH_4)_6Mo_7O_{24}.4H_2O$], 113.3 g of ammonium metavanadate ($NH_4VO_3$) and 153.4 g of telluric acid ($H_6TeO_6$) were added to 2,300 g of water, and the resultant mixture was heated to about 60° C. while stirring, to obtain a solution, and the obtained solution was cooled to about 30° C., to thereby obtain aqueous mixture A-6.

62.9 g of a niobic acid ($Nb_2O_5.nH_2O$) ($Nb_2O_5$ content: 76.6% by weight) and 137.2 g of oxalic acid ($H_2C_2O_4.2H_2O$) were added to 530 g of water, and the resultant mixture was heated to about 60° C. while stirring, followed by cooling to about 30° C., to thereby obtain aqueous mixture B-6. In the obtained aqueous mixture B-6, the [$H_2C_2O_4$:Nb] molar ratio was 3.0.

26.1 g of ytterbium nitrate [$Yb(NO_3)_3.4H_2O$] was dissolved in 130 g of water, to thereby obtain aqueous mixture C-6.

To aqueous mixture A-6 were added, while stirring, aqueous mixtures B-6 and C-6 and 1,000 g of silica sol S-1 prepared in Reference Example, to thereby obtain an aqueous mixture of raw materials.

The aqueous mixture of raw materials was subjected to spray drying using a centrifugation type spray-drying apparatus under conditions wherein the inlet and outlet temperatures of the apparatus were 240° C. and 145° C., respectively, to thereby obtain a dried, spherical particulate catalyst precursor.

The obtained catalyst precursor was pre-calcined at 275° C. for 2 hours in an atmosphere of air to obtain an oxide. 85 g of the obtained oxide was charged into a stainless steel (SUS) tube having an inner diameter of 1 inch, and then calcined at 600° C. for 2 hours under a stream of nitrogen gas at a flow rate of 150 Ncc/min, to thereby obtain a catalyst.

The alkali metal content of the obtained catalyst was determined by the same method as in Example 1. It was found that the alkali metal content of the catalyst was 0.0007 in terms of the atomic ratio of an alkali metal, relative to molybdenum.

(Ammoxidation of propane)

An ammoxidation was performed in the presence of the obtained catalyst under the same conditions as in Example 1. The results of the ammoxidation are shown in Table 1.

EXAMPLE 7

(Preparation of an ammoxidation catalyst)

An ammoxidation catalyst, which comprises a compound oxide and a silica carrier having supported thereon the compound oxide, wherein the silica carrier is present in an amount of 30% by weight in terms of $SiO_2$, based on the total weight of the compound oxide and the silica carrier, and wherein the compound oxide is represented by the formula:

$$Mo_{1.0}V_{0.32}Nb_{0.12}Te_{0.22}Yb_{0.02}O_n,$$

was prepared as follows.

534.1 g of ammonium heptamolybdate [$(NH_4)_6Mo_7O_{24}.4H_2O$], 113.3 g of ammonium metavanadate ($NH_4VO_3$) and 153.4 g of telluric acid ($H_6TeO_6$) were added to 2,300 g of water, and the resultant mixture was heated to about 60° C. while stirring, to obtain a solution, and the obtained solution was cooled to about 30° C., to thereby obtain aqueous mixture A-7.

62.9 g of a niobic acid ($Nb_2O_5.nH_2O$) ($Nb_2O_5$ content: 76.6% by weight) and 137.2 g of oxalic acid ($H_2C_2O_4.2H_2O$) were added to 530 g of water, and the resultant mixture was heated to about 60° C. while stirring, followed by cooling to about 30° C., to thereby obtain aqueous mixture B-7. In the obtained aqueous mixture B-7, the [$H_2C_2O_4$:Nb] molar ratio was 3.0.

26.1 g of ytterbium nitrate [$Yb(NO_3)_3.H_2O$] was dissolved in 130 g of water, to thereby obtain aqueous mixture C-7.

To aqueous mixture A-7 were added, while stirring, aqueous mixtures B-7 and C-7, an aqueous sodium nitrate solution composed of 10 g of water and 1.10 g of sodium nitrate ($NaNO_3$), and 1,000 g of silica sol S-1 prepared in Reference Example, to thereby obtain an aqueous mixture of raw materials.

The aqueous mixture of raw materials was subjected to spray drying using a centrifugation type spray-drying apparatus under conditions wherein the inlet and outlet temperatures of the apparatus were 240° C. and 145° C., respectively, to thereby obtain a dried, spherical particulate catalyst precursor.

The obtained catalyst precursor was pre-calcined at 275° C. for 2 hours in an atmosphere of air to obtain an oxide. 85 g of the obtained oxide was charged into a stainless steel (SUS) tube having an inner diameter of 1 inch, and then calcined at 600° C. for 2 hours under a stream of nitrogen gas at a flow rate of 150 Ncc/min, to thereby obtain a catalyst.

The alkali metal content of the obtained catalyst was determined by the same method as in Example 1. It was found that the alkali metal content of the catalyst was 0.0049 in terms of the atomic ratio of an alkali metal, relative to molybdenum.

(Ammoxidation of propane)

An ammoxidation was performed in the presence of the obtained catalyst under the same conditions as in Example 1. The results of the ammoxidation are shown in Table 1.

EXAMPLE 8

(Preparation of an ammoxidation catalyst)

An ammoxidation catalyst, which comprises a compound oxide and a silica carrier having supported thereon the compound oxide, wherein the silica carrier is present in an amount of 30% by weight in terms of $SiO_2$, based on the total weight of the compound oxide and the silica carrier, and wherein the compound oxide is represented by the formula:

$$Mo_{1.0}V_{0.32}Nb_{0.12}Te_{0.22}Yb_{0.02}O_n,$$

was prepared as follows.

534.1 g of ammonium heptamolybdate [$(NH_4)_6Mo_7O_{24}.4H_2O$], 113.3 g of ammonium metavanadate ($NH_4VO_3$) and 153.4 g of telluric acid ($H_6TeO_6$) were added to 2,300 g of water, and the resultant mixture was heated to about 60° C. while stirring, to obtain a solution, and the obtained solution was cooled to about 30° C., to thereby obtain aqueous mixture A-8.

62.9 g of a niobic acid ($Nb_2O_5.nH_2O$) ($Nb_2O_5$ content: 76.6% by weight) and 137.2 g of oxalic acid ($H_2C_2O_4.2H_2O$) were added to 530 g of water, and the resultant mixture was heated to about 60° C. while stirring, followed by cooling to about 30° C., to thereby obtain aqueous mixture B-8. In the obtained aqueous mixture B-8, the [$H_2C_2O_4$:Nb] molar ratio was 3.0.

26.1 g of ytterbium nitrate [$Yb(NO_3)_3 \cdot 4H_2O$] was dissolved in 130 g of water, to thereby obtain aqueous mixture C-8.

To 1,000 g of silica sol S-1 prepared in Reference Example were added an aqueous sodium nitrate solution composed 10 g of water and 0.15 g of sodium nitrate ($NaNO_3$), to thereby obtain silica sol S-8 having an alkali metal content of 0.00042 in terms of the atomic ratio of an alkali metal, relative to silicon.

To aqueous mixture A-8 were added aqueous mixtures B-8 and C-8 and all of silica sol S-8 while stirring, to thereby obtain an aqueous mixture of raw materials.

The aqueous mixture of raw materials was subjected to spray drying using a centrifugation type spray drying apparatus under conditions wherein the inlet and outlet temperatures of the apparatus were 240° C. and 145° C., respectively, to thereby obtain a dried, spherical particulate catalyst precursor.

The obtained catalyst precursor was pre-calcined at 275° C. for 2 hours in an atmosphere of air to obtain an oxide. 85 g of the obtained oxide was charged into a stainless steel (SUS) tube having an inner diameter of 1 inch, and then calcined at 600° C. for 2 hours under a stream of nitrogen gas at a flow rate of 150 Ncc/min, to thereby obtain a catalyst.

The alkali metal content of the obtained catalyst was determined by the same method as in Example 1. It was found that the alkali metal content of the catalyst was 0.0012 in terms of the atomic ratio of an alkali metal, relative to molybdenum.

(Ammoxidation of propane)

An ammoxidation was performed in the presence of the obtained catalyst under the same conditions as in Example 1. The results of the ammoxidation are shown in Table 1.

EXAMPLE 9

(Preparation of an ammoxidation catalyst)

An ammoxidation catalyst, which comprises a compound oxide and a silica carrier having supported thereon the compound oxide, wherein the silica carrier is present in an amount of 30% by weight in terms of $SiO_2$, based on the total weight of the compound oxide and the silica carrier, and wherein the compound oxide is represented by the formula:

$$Mo_{1.0}V_{0.32}Nb_{0.12}Te_{0.22}Yb_{0.02}O_n,$$

was prepared in substantially the same manner as in Example 8, except that, instead of 0.15 g of sodium nitrate, use was made of 1.10 g of sodium nitrate to thereby obtain silica sol S-9 having an alkali metal content of 0.00264 in terms of the atomic ratio of an alkali metal, relative to silicon (silica sol S-9 was used instead of silica sol S-8).

The alkali metal content of the obtained catalyst was determined by the same method as in Example 1. It was found that the alkali metal content of the catalyst was 0.0050 in terms of the atomic ratio of an alkali metal, relative to molybdenum.

(Ammoxidation of propane)

An ammoxidation was performed in the presence of the obtained catalyst under the same conditions as in Example 1. The results of the ammoxidation are shown in Table 1.

COMPARATIVE EXAMPLE 6

(Preparation of an ammoxidation catalyst)

An ammoxidation catalyst, which comprises a compound oxide and a silica carrier having supported thereon the compound oxide, wherein the silica carrier is present in an amount of 30% by weight in terms of $SiO_2$, based on the total weight of the compound oxide and the silica carrier, and wherein the compound oxide is represented by the formula:

$$Mo_{1.0}V_{0.32}Nb_{0.12}Te_{0.22}Yb_{0.02}O_n,$$

was prepared in substantially the same manner as in Example 8, except that, instead of an aqueous sodium nitrate solution composed of 10 g of water and 0.15 g of sodium nitrate, use was made of an aqueous sodium nitrate solution composed of 30 g of water and 4.80 g of sodium nitrate, to thereby obtain a silica sol having an alkali metal content of 0.0113 in terms of the atomic ratio of an alkali metal, relative to silicon (this silica sol was used instead of silica sol S-8).

The alkali metal content of the obtained catalyst was determined by the same method as in Example 1. It was found that the alkali metal content of the catalyst was 0.0192 in terms of the atomic ratio of an alkali metal, relative to molybdenum.

(Ammoxidation of propane)

An ammoxidation was performed in the presence of the obtained catalyst under the same conditions as in Example 1. The results of the ammoxidation are shown in Table 1.

COMPARATIVE EXAMPLE 7

(Preparation of an ammoxidation catalyst)

An ammoxidation catalyst, which comprises a compound oxide and a silica carrier having supported thereon the compound oxide, wherein the silica carrier is present in an amount of 30% by weight in terms of $SiO_2$, based on the total weight of the compound oxide and the silica carrier, and wherein the compound oxide is represented by the formula:

$$Mo_{1.0}V_{0.32}Nb_{12}Te_{0.22}Yb_{0.02}O_n,$$

was prepared in substantially the same manner as in Example 6, except that, instead of 1,000 g of silica sol S-1, use was made of 1,500 g of a silica sol (ST-20, manufactured and sold by Nissan Chemical Industries, LTD., Japan) which has an $SiO_2$ content of 20% by weight and an alkali metal content of 0.0155 in terms of the atomic ratio of an alkali metal, relative to silicon.

The alkali metal content of the obtained catalyst was determined by the same method as in Example 1. It was found that the alkali metal content of the catalyst was 0.0262 in terms of the atomic ratio of an alkali metal, relative to molybdenum.

(Ammoxidation of propane)

An ammoxidation was performed in the presence of the obtained catalyst under the same conditions as in Example 1. The results of the ammoxidation are shown in Table 1.

EXAMPLE 10

(Preparation of an ammoxidation catalyst)

An ammoxidation catalyst, which comprises a compound oxide and a silica carrier having supported thereon the compound oxide, wherein the silica carrier is present in an amount of 30% by weight in terms of $SiO_2$, based on the total weight of the compound oxide and the silica carrier, and wherein the compound oxide is represented by the formula:

$$Mo_{1.0}V_{0.32}Nb_{0.12}Te_{0.22}Yb_{0.02}O_n,$$

was prepared as follows.

534.1 g of ammonium heptamolybdate [$(NH_4)_6Mo_7O_{24}\cdot 4H_2O$], 113.3 g of ammonium metavanadate ($NH_4VO_3$) and 153.4 g of telluric acid ($H_6TeO_6$) were added to 2,300 g of water, and the resultant mixture was heated to about 60° C. while stirring, to obtain a solution, and the obtained solution was cooled to about 30° C., to thereby obtain aqueous mixture A-10.

62.9 g of a niobic acid ($Nb_2O_5 \cdot nH_2O$) ($Nb_2O_5$ content: 76.6% by weight) and 137.2 g of oxalic acid ($H_2C_2O_4 \cdot 2H_2O$) were added to 530 g of water, and the resultant mixture was heated to about 60° C. while stirring, followed by cooling to about 30° C., to thereby obtain aqueous mixture B-10. In the obtained aqueous mixture B-10, the [$H_2C_2O_4$:Nb] molar ratio was 3.0.

26.1 g of ytterbium nitrate [$Yb(NO_3)_3 \cdot 4H_2O$] was dissolved in 130 g of water, to thereby obtain aqueous mixture C-10.

A silica sol having an $SiO_2$ content of 30% by weight and an alkali metal content of 0.0323 in terms of the atomic ratio of an alkali metal, relative to silicon, was passed through a hydrogen-type strongly acidic cation exchange resin, to thereby obtain silica sol S-10 having an $SiO_2$ content of 30% by weight and an alkali metal content of 0.0026 in terms of the atomic ratio of an alkali metal, relative to silicon.

To aqueous mixture A-10 were added aqueous mixtures B-10 and C-10 and 1,000 g of silica sol S-10 while stirring, to thereby obtain an aqueous mixture of raw materials.

The aqueous mixture of raw materials was subjected to spray drying using a centrifugation type spray-drying apparatus under conditions wherein the inlet and outlet temperatures of the apparatus were 240° C. and 145° C., respectively, to thereby obtain a dried, spherical particulate catalyst precursor.

The obtained catalyst precursor was pre-calcined at 275° C. for 2 hours in an atmosphere of air to obtain an oxide. 85 g of the obtained oxide was charged into a stainless steel (SUS) tube having an inner diameter of 1 inch, and then calcined at 600° C. for 2 hours under a stream of nitrogen gas at a flow rate of 150 Ncc/min, to thereby obtain a catalyst.

The alkali metal content of the obtained catalyst was determined by the same method as in Example 1. It was found that the alkali metal content of the catalyst was 0.0051 in terms of the atomic ratio of an alkali metal, relative to molybdenum.

(Ammoxidation of propane)

An ammoxidation was performed in the presence of the obtained catalyst under the same conditions as in Example 1. The results of the ammoxidation are shown in Table 1.

EXAMPLE 11
(Preparation of an ammoxidation catalyst)

An ammoxidation catalyst, which comprises a compound oxide and a silica carrier having supported thereon the compound oxide, wherein the silica carrier is present in an amount of 30% by weight in terms of $SiO_2$, based on the total weight of the compound oxide and the silica carrier, and wherein the compound oxide is represented by the formula:

$$Mo_{1.0}V_{0.32}Nb_{0.12}Te_{0.22}Yb_{0.02}O_n,$$

was prepared as follows.

534.1 g of ammonium heptamolybdate [$(NH_4)_6Mo_7O_{24}\cdot 4H_2O$], 113.3 g of ammonium metavanadate ($NH_4VO_3$) and 153.4 g of telluric acid ($H_6TeO_6$) were added to 2,300 g of water, and the resultant mixture was heated to about 60° C. while stirring, to obtain a solution, and the obtained solution was cooled to about 30° C., to thereby obtain aqueous mixture A-11.

62.9 g of a niobic acid ($Nb_2O_5 \cdot nH_2O$) ($Nb_2O_5$ content: 76.6% by weight) and 228.6 g of oxalic acid ($H_2C_2O_4 \cdot 2H_2O$) were added to 530 g of water, and the resultant mixture was heated to about 60° C. while stirring, followed by cooling to about 30° C., to thereby obtain aqueous mixture B-11. In the obtained aqueous mixture B-11, the [$H_2C_2O_4$:Nb] molar ratio was 5.0.

26.1 g of ytterbium nitrate [$Yb(NO_3)_3 \cdot 4H_2O$] was dissolved in 130 g of water, to thereby obtain aqueous mixture C-11.

An aqueous sodium nitrate solution composed of 10 g of water and 1.10 g of sodium nitrate ($NaNO_3$) was added to 1,000 g of silica sol S-1 prepared in Reference Example, to thereby obtain silica sol S-11 having an alkali metal content of 0.00264 in terms of the atomic ratio of an alkali metal, relative to silicon.

To aqueous mixture A-11 were added aqueous mixtures B-11 and C-11 and all of silica sol S-11 while stirring, to thereby obtain an aqueous mixture of raw materials.

The aqueous mixture of raw materials was subjected to spray drying using a centrifugation type spray-drying apparatus under conditions wherein the inlet and outlet temperatures of the apparatus were 240° C. and 145° C., respectively, to thereby obtain a dried, spherical particulate catalyst precursor.

The obtained catalyst precursor was pre-calcined at 275° C. for 2 hours in an atmosphere of air to obtain an oxide. 85 g of the obtained oxide was charged into a stainless steel (SUS) tube having an inner diameter of 1 inch, and then calcined at 600° C. for 2 hours under a stream of nitrogen gas at a flow rate of 150 Ncc/min, to thereby obtain a catalyst.

The alkali metal content of the obtained catalyst was determined by the same method as in Example 1. It was found that the alkali metal content of the catalyst was 0.0054 in terms of the atomic ratio of an alkali metal, relative to molybdenum.

(Ammoxidation of propane)

An ammoxidation was performed in the presence of the obtained catalyst under the same conditions as in Example 1. The results of the ammoxidation are shown in Table 1.

COMPARATIVE EXAMPLE 8
(Preparation of an ammoxidation catalyst)

An ammoxidation catalyst, which comprises a compound oxide and a silica carrier having supported thereon the compound oxide, wherein the silica carrier is present in an amount of 30% by weight in terms of $SiO_2$, based on the total weight of the compound oxide and the silica carrier, and wherein the compound oxide is represented by the formula:

$$Mo_{1.0}V_{0.32}Nb_{0.12}Te_{0.22}Yb_{0.02}O_n,$$

was prepared in substantially the same manner as in Example 11, except that, instead of silica sol S-11, use was made of 1,500 g of a silica sol (ST-20, manufactured and sold by Nissan Chemical Industries, LTD., Japan) which has an $SiO_2$ content of 20% by weight and an alkali metal content of 0.0155 in terms of the atomic ratio of an alkali metal, relative to silicon.

The alkali metal content of the obtained catalyst was determined by the same method as in Example 1. It was found that the alkali metal content of the catalyst was 0.0270 in terms of the atomic ratio of an alkali metal, relative to molybdenum.

(Ammoxidation of propane)

An ammoxidation was performed in the presence of the obtained catalyst under the same conditions as in Example 1. The results of the ammoxidation are shown in Table 1.

EXAMPLE 12

(Preparation of an ammoxidation catalyst)

An ammoxidation catalyst, which comprises a compound oxide and a silica carrier having supported thereon the compound oxide, wherein the silica carrier is present in an amount of 40% by weight in terms of $SiO_2$, based on the total weight of the compound oxide and the silica carrier, and wherein the compound oxide is represented by the formula:

$$Mo_{1.0}V_{0.32}Nb_{0.12}Te_{0.22}Yb_{0.02}O_n,$$

was prepared as followed.

457.8 g of ammonium heptamolybdate [$(NH_4)_6Mo_7O_{24}.4H_2O$], 97.1 g of ammonium metavanadate ($NH_4VO_3$) and 131.5 g of telluric acid ($H_6TeO_6$) were added to 2,000 g of water, and the resultant mixture was heated to about 60° C. while stirring, to obtain a solution, and the obtained solution was cooled to about 30° C., to thereby obtain aqueous mixture A-12.

53.9 g of a niobic acid ($Nb_2O_5.nH_2O$) ($Nb_2O_5$ content: 76.6% by weight) and 117.5 g of oxalic acid ($H_2C_2O_4.2H_2O$) were added to 450 g of water, and the resultant mixture was heated to about 60° C. while stirring, followed by cooling to about 30° C., to thereby obtain aqueous mixture B-12. In the obtained aqueous mixture B-12, the [$H_2C_2O_4$:Nb] molar ratio was 3.0.

22.4 g of ytterbium nitrate [$Yb(NO_3)_3.4H_2O$] was dissolved in 110 g of water, to thereby obtain aqueous mixture C-12.

An aqueous sodium nitrate solution composed of 10 g of water and 0.20 g of sodium nitrate ($NaNO_3$) was added to 1,333.3 g of silica sol S-1 prepared in Reference Example, to thereby obtain silica sol S-12 having an alkali metal content of 0.00042 in terms of the atomic ratio of an alkali metal, relative to silicon.

To aqueous mixture A-12 were added aqueous mixtures B-12 and C-12 and all of silica sol S-12 while stirring, to thereby obtain an aqueous mixture of raw materials.

The aqueous mixture of raw materials was subjected to spray drying using a centrifugation type spray drying apparatus under conditions wherein the inlet and outlet temperatures of the apparatus were 240° C. and 145° C., respectively, to thereby obtain a dried, spherical particulate catalyst precursor.

The obtained catalyst precursor was pre-calcined at 275° C. for 2 hours in an atmosphere of air to obtain an oxide. 85 g of the obtained oxide was charged into a stainless steel (SUS) tube having an inner diameter of 1 inch, and then calcined at 600° C. for 2 hours under a stream of nitrogen gas at a flow rate of 150 Ncc/min, to thereby obtain a catalyst.

The alkali metal content of the obtained catalyst was determined by the same method as in Example 1. It was found that the alkali metal content of the catalyst was 0.0016 in terms of the atomic ratio of an alkali metal, relative to molybdenum.

(Ammoxidation of propane)

An ammoxidation was performed in the presence of the obtained catalyst under the same conditions as in Example 1. The results of the ammoxidation are shown in Table 1.

COMPARATIVE EXAMPLE 9

(Preparation of an ammoxidation catalyst)

An ammoxidation catalyst, which comprises a compound oxide and a silica carrier having supported thereon the compound oxide, wherein the silica carrier is present in an amount of 40% by weight in terms of $SiO_2$, based on the total weight of the compound oxide and the silica carrier, and wherein the compound oxide is represented by the formula:

$$Mo_{1.0}V_{0.32}Nb_{0.12}Te_{0.22}Yb_{0.02}O_n,$$

was prepared in substantially the same manner as in Example 12, except that, instead of silica sol S-12, use was made of 2,000 g of a silica sol (ST-20, manufactured and sold by Nissan Chemical Industries, LTD., Japan) which has an $SiO_2$ content of 20% by weight and an alkali metal content of 0.0155 in terms of the atomic ratio of an alkali metal, relative to silicon.

The alkali metal content of the obtained catalyst was determined by the same method as in Example 1. It was found that the alkali metal content of the catalyst was 0.040 in terms of the atomic ratio of an alkali metal, relative to molybdenum.

(Ammoxidation of propane)

An ammoxidation was performed in the presence of the obtained catalyst under the same conditions as in Example 1. The results of the ammoxidation are shown in Table 1.

TABLE 1

| | Composition of ammoxidation catalyst[1] | Alkali metal content of catalyst[2] | Conversion of propane (%) | Selectivity for acrylonitrile (%) | Yield of acrylonitrile (%) |
|---|---|---|---|---|---|
| Ex. 1 | $Mo_{1.0}V_{0.32}Nb_{0.12}Te_{0.22}O_n/SiO_2$ | 0.0007 | 85.1 | 61.9 | 52.7 |
| Ex. 2 | $Mo_{1.0}V_{0.32}Nb_{0.12}Te_{0.22}O_n/SiO_2$ | 0.0048 | 80.0 | 62.6 | 50.1 |
| Ex. 3 | $Mo_{1.0}V_{0.32}Nb_{0.12}Te_{0.22}O_n/SiO_2$ | 0.0069 | 79.8 | 62.4 | 49.8 |
| Comp. Ex. 1 | $Mo_{1.0}V_{0.32}Nb_{0.12}Te_{0.22}O_n/SiO_2$ | 0.0125 | 77.2 | 58.9 | 45.5 |
| Comp. Ex. 2 | $Mo_{1.0}V_{0.32}Nb_{0.12}Te_{0.22}O_n/SiO_2$ | 0.0263 | 55.2 | 27.2 | 15.0 |
| Comp. Ex. 3 | $Mo_{1.0}V_{0.32}Nb_{0.12}Te_{0.22}O_n/SiO_2$ | 0.0265 | 54.6 | 33.9 | 18.5 |
| Ex. 4 | $Mo_{1.0}V_{0.32}Nb_{0.12}Te_{0.22}O_n/SiO_2$ | 0.0013 | 84.9 | 61.2 | 52.0 |
| Ex. 5 | $Mo_{1.0}V_{0.32}Nb_{0.12}Te_{0.22}O_n/SiO_2$ | 0.0069 | 79.5 | 63.3 | 50.3 |
| Comp. Ex. 4 | $Mo_{1.0}V_{0.32}Nb_{0.12}Te_{0.22}O_n/SiO_2$ | 0.0264 | 55.7 | 30.0 | 16.7 |
| Comp. Ex. 5 | $Mo_{1.0}V_{0.32}Nb_{0.12}Te_{0.22}O_n/SiO_2$ | 0.0266 | 56.4 | 29.8 | 16.8 |

TABLE 1-continued

| | Composition of ammoxidation catalyst[1] | Alkali metal content of catalyst[2] | Conversion of propane (%) | Selectivity for acrylonitrile (%) | Yield of acrylonitrile (%) |
|---|---|---|---|---|---|
| Ex. 6 | $Mo_{1.0}V_{0.32}Nb_{0.12}Te_{0.22}Yb_{0.02}O_n/SiO_2$ | 0.0007 | 87.9 | 62.4 | 54.9 |
| Ex. 7 | $Mo_{1.0}V_{0.32}Nb_{0.12}Te_{0.22}Yb_{0.02}O_n/SiO_2$ | 0.0049 | 86.6 | 61.2 | 53.0 |
| Ex. 8 | $Mo_{1.0}V_{0.32}Nb_{0.12}Te_{0.22}Yb_{0.02}O_n/SiO_2$ | 0.0012 | 87.6 | 62.4 | 54.7 |
| Ex. 9 | $Mo_{1.0}V_{0.32}Nb_{0.12}Te_{0.22}Yb_{0.02}O_n/SiO_2$ | 0.0050 | 82.1 | 64.9 | 53.3 |
| Comp. Ex. 6 | $Mo_{1.0}V_{0.32}Nb_{0.12}Te_{0.22}Yb_{0.02}O_n/SiO_2$ | 0.0192 | 68.5 | 47.4 | 32.5 |
| Comp. Ex. 7 | $Mo_{1.0}V_{0.32}Nb_{0.12}Te_{0.22}Yb_{0.02}O_n/SiO_2$ | 0.0262 | 59.0 | 34.7 | 20.5 |
| Ex. 10 | $Mo_{1.0}V_{0.32}Nb_{0.12}Te_{0.22}Yb_{0.02}O_n/SiO_2$ | 0.0051 | 85.9 | 61.9 | 53.2 |
| Ex. 11 | $Mo_{1.0}V_{0.32}Nb_{0.12}Te_{0.22}Yb_{0.02}O_n/SiO_2$ | 0.0054 | 80.6 | 62.7 | 50.5 |
| Comp. Ex. 8 | $Mo_{1.0}V_{0.32}Nb_{0.12}Te_{0.22}Yb_{0.02}O_n/SiO_2$ | 0.0270 | 60.3 | 29.4 | 17.7 |
| Ex. 12 | $Mo_{1.0}V_{0.32}Nb_{0.12}Te_{0.22}Yb_{0.02}O_n/SiO_2$ | 0.0016 | 84.6 | 63.3 | 53.5 |
| Comp. Ex. 9 | $Mo_{1.0}V_{0.32}Nb_{0.12}Te_{0.22}Yb_{0.02}O_n/SiO_2$ | 0.040 | 50.9 | 23.2 | 11.8 |

Note
[1] In Examples 1 to 11 and Comparative Examples 1 to 8, the amount of the silica carrier ($SiO_2$) is 30 wt %.
In Example 12 and Comparative Example 9, the amount of $SiO_2$ is 40 wt %.
[2] The alkali metal content is expressed in terms of the atomic ratio of an alkali metal, relative to molybdenum (Mo).

INDUSTRIAL APPLICABILITY

The ammoxidation catalyst of the present invention, which comprises a silica carrier having supported thereon a compound oxide of Mo, V, Nb and at least one element selected from the group consisting of Te and Sb and wherein the alkali metal content of the ammoxidation catalyst is extremely small or substantially zero, is not only effective for producing acrylonitrile or methacrylonitrile in high yield, as compared to the yield achieved by conventional ammoxidation catalysts containing a silica carrier, but also can be easily produced, so that the catalyst of the present invention is advantageous from a commercial viewpoint.

What is claimed is:

1. An ammoxidation catalyst for use in producing acrylonitrile or methacrylonitrile from propane or isobutane by ammoxidation in the gaseous phase, which comprises a compound oxide and a silica carrier having supported thereon said compound oxide, wherein said catalyst has an alkali metal content of 0.01 or less in terms of the atomic ratio of an alkali metal, relative to molybdenum, wherein said catalyst is produced by a method comprising:

providing an aqueous mixture of a silica sol and compounds of molybdenum, vanadium, niobium, at least one element selected from the group consisting of tellurium and antimony, and optionally at least one element selected from the group consisting of ytterbium, dysprosium, erbium, cerium, neodymium, samarium, lanthanum, praseodymium, europium, gadolinium, terbium, holmium, thulium, lutetium, scandium, tungsten, chromium, tantalum, titanium, zirconium, hafnium, manganese, rhenium, iron, ruthenium, cobalt, rhodium, nickel, palladium, platinum, copper, silver, zinc, boron, aluminum, gallium, indium, germanium, tin, lead, phosphorus, bismuth and alkaline earth metals;

drying said aqueous mixture, to thereby obtain a catalyst precursor; and calcining the catalyst precursor in an atmosphere of inert gas which is substantially free of molecular oxygen, said silica sol having an alkali metal content of 0.007 or less in terms of the atomic ratio of an alkali metal, relative to silicon.

2. The catalyst according to claim 1, wherein said silica carrier is present in an amount of from 25 to 70 % by weight in terms of $SiO_2$, based on the total weight of said compound oxide and said silica carrier, and wherein said compound oxide is represented by the following formula (1):

$$Mo_{1.0}V_aNb_bX_cZ_dO_n \qquad (1)$$

wherein:

X is at least one element selected from the group consisting of tellurium and antimony;

Z is at least one element selected from the group consisting of ytterbium, dysprosium, erbium, cerium, neodymium, samarium, lanthanum, praseodymium, europium, gadolinium, terbium, holmium, thulium, lutetium, scandium, tungsten, chromium, tantalum, titanium, zirconium, hafnium, manganese, rhenium, iron, ruthenium, cobalt, rhodium, nickel, palladium, platinum, copper, silver, zinc, boron, aluminum, gallium, indium, germanium, tin, lead, phosphorus, bismuth and alkaline earth metals; and a, b, c, d and n are, respectively, the atomic ratios of vanadium, niobium, X, Z and oxygen, relative to molybdenum, wherein:

$0.1 \leq a \leq 1.0$;

$0.01 \leq b \leq 1.0$;

$0.01 \leq c \leq 1.0$;

$0 \leq d \leq 0.1$; and n is a number determined by and consistent with the valence requirements of the other elements present in the compound oxide of formula (1).

3. The catalyst according to claim 2, wherein X in formula (1) is tellurium.

4. The catalyst according to claim 2 or 3, wherein Z in formula (1) is at least one element selected from the group consisting of ytterbium, dysprosium and erbium.

5. The catalyst according to claim 1 or 2, which has an alkali metal content of 0.007 or less in terms of the atomic ratio of an alkali metal, relative to molybdenum.

6. The catalyst according to claim 1, wherein said niobium compound is in the form of a niobium-containing aqueous solution comprising water having dissolved therein a dicarboxylic acid and a niobium compound, wherein the molar ratio of the dicarboxylic acid to niobium is in the range of from 2 to 4.

7. A process for producing acrylonitrile or methacrylonitrile, which comprises reacting propane or isobutane with ammonia and molecular oxygen in the gaseous phase in the presence of an ammoxidation catalyst comprising a compound oxide and a silica carrier having supported thereon said compound oxide, wherein said catalyst has an alkali metal content of 0.01 or less in terms of the atomic ratio of an alkali metal, relative to molybdenum, wherein said catalyst is produced by a method comprising:

providing an aqueous mixture of a silica sol and compounds of molybdenum, vanadium, niobium, at least one element selected from the group consisting of tellurium and antimony, and optionally at least one element selected from the group consisting of ytterbium, dysprosium, erbium, cerium, neodymium, samarium, lanthanum, praseodymium, europium, gadolinium, terbium, holmium, thulium, lutetium, scandium, tungsten, chromium, tantalum, titanium, zirconium, hafnium, manganese, rhenium, iron, ruthenium, cobalt, rhodium, nickel, palladium, platinum, copper, silver, zinc, boron, aluminum, gallium, indium, germanium, tin, lead, phosphorus, bismuth and alkaline earth metals;

drying said aqueous mixture, to thereby obtain a catalyst precursor; and calcining the catalyst precursor in an atmosphere of inert gas which is substantially free of molecular oxygen, said silica sol having an alkali metal content of 0.007 or less in terms of the atomic ratio of an alkali metal, relative to silicon.

8. The process according to claim 7, wherein, in said catalyst, said silica carrier is present in an amount of from 25 to 70% by weight in terms of $SiO_2$, based on the total weight of said compound oxide and said silica carrier, and said compound oxide is represented by the following formula (1):

$$Mo_{1.0}V_aNb_bX_cZ_dO_n \qquad (1)$$

wherein:

X is at least one element selected from the group consisting of tellurium and antimony;

Z is at least one element selected from the group consisting of ytterbium, dysprosium, erbium, cerium, neodymium, samarium, lanthanum, praseodymium, europium, gadolinium, terbium, holmium, thulium, lutetium, scandium, tungsten, chromium, tantalum, titanium, zirconium, hafnium, manganese, rhenium, iron, ruthenium, cobalt, rhodium, nickel, palladium, platinum, copper, silver, zinc, boron, aluminum, gallium, indium, germanium, tin, lead, phosphorus, bismuth and alkaline earth metals; and a, b, c, d and n are, respectively, the atomic ratios of vanadium, niobium, X, Z and oxygen, relative to molybdenum, wherein:

$0.1 \leq a \leq 1.0$;

$0.01 \leq b \leq 1.0$;

$0.01 \leq c \leq 1.0$;

$0 \leq d \leq 0.1$; and n is a number determined by and consistent with the valence requirements of the other elements present in the compound oxide of formula (1).

9. The process according to claim 8, wherein X in formula (1) is tellurium.

10. The process according to claim 8 or 9, wherein Z in formula (1) is at least one element selected from the group consisting of ytterbium, dysprosium and erbium.

11. The process according to claim 7 or 8, wherein said catalyst has an alkali metal content of 0.007 or less in terms of the atomic ratio of an alkali metal, relative to molybdenum.

12. The process according to claim 7, wherein said niobium compound is in the form of a niobium containing aqueous solution comprising water having dissolved therein a dicarboxylic acid and a niobium compound, wherein the molar ratio of the dicarboxylic acid to niobium is in the range of from 2 to 4.

* * * * *